(12) United States Patent
Glorieux et al.

(10) Patent No.: US 12,186,209 B2
(45) Date of Patent: Jan. 7, 2025

(54) METHOD FOR MANUFACTURING A PROSTHESIS SOCKET

(71) Applicant: OTTOBOCK SE & CO. KGAA, Duderstadt (DE)

(72) Inventors: Dries Glorieux, Lommel (BE); Kai-Hendrik Bussiek-Cillien, Gottingen (DE); Mark Schönemeier, Gottingen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 326 days.

(21) Appl. No.: 17/636,573

(22) PCT Filed: Aug. 11, 2020

(86) PCT No.: PCT/EP2020/072509
§ 371 (c)(1),
(2) Date: Feb. 18, 2022

(87) PCT Pub. No.: WO2021/032538
PCT Pub. Date: Feb. 25, 2021

(65) Prior Publication Data
US 2022/0280313 A1   Sep. 8, 2022

(30) Foreign Application Priority Data

Aug. 20, 2019   (DE) .................. 10 2019 122 374.1

(51) Int. Cl.
*A61F 2/50*   (2006.01)
*A61F 2/76*   (2006.01)
*A61B 5/00*   (2006.01)

(52) U.S. Cl.
CPC .............. *A61F 2/5046* (2013.01); *A61F 2/76* (2013.01); *A61B 5/4851* (2013.01);
(Continued)

(58) Field of Classification Search
CPC ........... A61B 5/4851; A61F 2002/5049; A61F 2002/505; A61F 2002/607;
(Continued)

(56) References Cited

U.S. PATENT DOCUMENTS 10,070,672 B2   9/2018  Simoes
10,650,604 B1*  5/2020  Moon .................. G06T 15/08
(Continued)

FOREIGN PATENT DOCUMENTS

CN   105877879 A   8/2016
CN   106687061 A   5/2017
(Continued)

OTHER PUBLICATIONS

International Search Report and Written Opinion issued in PCT/EP2020/072509, Feb. 25, 2021, 12 pgs.
(Continued)

*Primary Examiner* — Vincent H Tran
(74) *Attorney, Agent, or Firm* — HOLLAND & HART LLP

(57) ABSTRACT

A method for manufacturing an orthopedic product for a body part of a patient is disclosed, the method comprising the following steps: a) providing body-part data containing information about an internal structure of the body part, b) detecting a current line of vision from which a user of the method sees the body part, c) displaying the body part data from the current line of vision by means of the display device so that the user sees the body part and the body part data superimposed, d) generating production data for the orthopedic device on the basis of the displayed data and e) providing an orthopedic product manufactured on the basis of the production data.

18 Claims, 2 Drawing Sheets

(52) U.S. Cl.
CPC . *A61F 2002/5049* (2013.01); *A61F 2002/762* (2013.01); *A61F 2002/763* (2013.01)

(58) Field of Classification Search
CPC .......... A61F 2002/762; A61F 2002/769; A61F 2002/7695; A61F 2/5046; A61F 2/76
See application file for complete search history.

(56) References Cited

U.S. PATENT DOCUMENTS

| | | |
|---|---|---|
| 2005/0119777 A1 | 6/2005 | Arbogast et al. |
| 2014/0063220 A1 | 3/2014 | Taylor |
| 2014/0300907 A1* | 10/2014 | Kimmel .................. G06T 7/62 |
| | | 356/625 |
| 2016/0263345 A1* | 9/2016 | Shuster ..................... A61F 2/72 |
| 2017/0025026 A1* | 1/2017 | Ortiz Catalan ......... G06F 3/017 |
| 2017/0290685 A1 | 10/2017 | Montez et al. |
| 2018/0235779 A1* | 8/2018 | Dudding ............... A61F 2/7812 |
| 2018/0368996 A1* | 12/2018 | Van Vliet .................. A61F 2/80 |
| 2019/0038374 A1* | 2/2019 | Abreu Carpinteiro ... A61F 2/76 |
| 2019/0231433 A1* | 8/2019 | Amanatullah ...... A61B 17/1703 |
| 2019/0365514 A1* | 12/2019 | Hasan .................. A61C 13/097 |
| 2020/0197195 A1* | 6/2020 | Saenz Espinoza .. A61B 5/0073 |
| 2021/0065911 A1* | 3/2021 | Goel ....................... G16H 50/20 |
| 2021/0121237 A1* | 4/2021 | Fanson .................. A61B 34/20 |
| 2021/0145608 A1* | 5/2021 | Herr ...................... A61B 8/0825 |

FOREIGN PATENT DOCUMENTS

| | | |
|---|---|---|
| CN | 108938155 A | 12/2018 |
| DE | 10 2014 006 690 A1 | 11/2015 |
| WO | WO 2007/144608 A2 | 12/2007 |
| WO | WO 2018/130691 A1 | 7/2018 |
| WO | WO 2019/157486 A1 | 8/2019 |

OTHER PUBLICATIONS

Search Report issued in Chinese Patent Application No. 202080058078. 2, 2 pgs.

* cited by examiner

METHOD FOR MANUFACTURING A PROSTHESIS SOCKET

CROSS REFERENCE TO RELATED APPLICATIONS

This is a national phase application of International Application No. PCT/EP2020/072509, filed 11 Aug. 2020, which claims the benefit of German Patent Application No. 10 2019 122 374.1, filed 20 Aug. 2019, the disclosures of which are incorporated herein, in their entireties, by this reference.

TECHNICAL FIELD

The invention relates to a method for producing an orthopedic product for a body part of a patient.

BACKGROUND

For the purposes of the present invention, orthopedic products refer particularly to orthoses and prostheses. Orthoses are products that brace, support, protect of restrict the freedom of movement of a patient's body part, such as a joint, to prevent excessive strain. Prostheses, on the other hand, replace body parts of the patient that do not or no longer exist.

In the following, a patient is understood to mean any user of the orthopedic product. It therefore refers to the wearer of the produced product.

Every orthopedic product is arranged on one body part of the patient. It does not necessarily have to come into contact with the patient's skin. For example, orthoses are often worn over clothing, so that this clothing, for example trousers, is located between the orthopedic product and the patient's skin. Nevertheless, a knee orthosis, for example, is attached to the patient's knee or leg. A prosthesis always features an interface element that is connected to an amputation stump or another body part, said interface element being attached to the respective body part. In the case of a leg prosthesis, for example, a prosthesis socket is used which represents the interface between the prosthesis and the amputation stump. In this case, the amputation stump would be the patient's body part.

A prosthesis socket for an amputation stump is usually produced from a rigid and inflexible material, such as a fiber-reinforced plastic, and forms an important component of the interface between the amputation stump and the prosthesis that is arranged on the prosthesis socket. Especially for leg prostheses that are to be arranged on an amputation stump, such as an upper leg stump, corresponding prosthesis sockets have been used for many years. However, the invention is not limited to these types of prosthesis socket. Prosthesis sockets of the type described here can also be used for arm prostheses or lower leg prostheses. Prosthesis sockets for leg amputees in particular are subjected to considerable loads during everyday use. When the patient is walking, their entire weight is on the prosthesis socket and thus especially on the amputation stump arranged in the prosthesis socket. It is therefore very important to adapt the prosthesis socket to the patient's individual conditions and needs as effectively as possible.

A number of different methods are therefore known from the prior art, with which the shape and design of the prosthesis socket are to be adapted to the amputation stump under load. To this end, an impression is usually made of the amputation stump in order to obtain a blank and base body on which the prosthesis socket is built. Creating an impression of the residual limb using plaster to create a negative mold of the residual limb still dominates. In addition to the low costs, this method has the advantage that experienced orthopedic technicians can already influence the shape of the later prosthesis socket by specifically shaping the amputation stump during plastering. This is especially advantageous if the later socket is to feature specific load-bearing zones.

To be able to apply as uniform a load as possible to the amputation stump, methods have increasingly been developed that apply uniform pressure to the amputation stump while the shape of the amputation stump is being assumed. For example, the residual limb is arranged in a volume filled with water, so that the water can exert a uniform pressure. As an alternative to a water bath, a volume filled with sand can be used. The disadvantage, however, is that such methods are more difficult to transport due to their design and can therefore barely be used in daily clinical practice.

Optical scanning methods, with which the amputation stump is measured by optical camera devices, are known from the prior art. However, even if such a method can be used, the amputation stump is only measured statically. It is generally not possible to capture data when the amputation stump is moving. Moreover, the scanning device often has to be manually guided around the body part to be captured, which is complex and less convenient. Furthermore, it is not usually possible to deform the amputation stump by hand, for example, by building up pressure and to capture the amputation stump deformed in such a manner.

The disadvantage of all of the specified methods known from the prior art is that, at most, the outer shape of the amputation stump is included in the shaping of the prosthesis socket. The positioning of areas that require special padding or relief is only possible through the experience of the orthopedic technician. It is very difficult to take into account highly individual requirements or conditions caused by special features of the amputation. Scanning methods also have the disadvantage that the user of the method, such as an orthopedic technician, cannot change and adjust the result of the scan directly on the residual limb. As a result, they lose the usually available possibility of shaping and adjusting the residual limb. It is possible to subsequently change and adjust the scan using an electronic data processing device, such as a computer, tablet or laptop, but this does not give the user the same haptic feedback as pressing and molding the residual limb.

A further disadvantage is that fact that the shaping of the amputation stump, as already explained, is only incorporated on the basis of static data, for example the outer shape of the unloaded residual limb. Therefore, a test socket is first created that must be tested on and worn by the patient. This checks whether the socket meets the requirements or whether changes are necessary. The shape of the test socket may have to be adapted to a dynamic situation if the test socket uncovers issues and suboptimal shapes. This is time-consuming and expensive.

In particular in the case of prosthesis sockets, but also with other orthopedic products such as orthoses, components or the entire products are ideally individually adapted to meet the patient's physical conditions. In many cases, this requires an exact measurement of the body part, which is associated with the problems specified above.

SUMMARY

The invention therefore aims to propose a method for producing an orthopedic product for a patient's body part that eliminates or at least mitigates these disadvantages.

The invention solves the problem by way of a method for producing an orthopedic product for a patient's body part, the method comprising the following steps:

a) providing body part data that contains information about the inner structure of the body part,
b) detecting a current direction of view from which a user of the method sees the body part,
c) presenting the body part data from the current direction of view by means of the display device, so that the user sees the body part and the body part data superimposed,
d) generating production data for the orthopedic product on the basis of the data displayed, and
e) providing an orthopedic product produced on the basis of the production data.

The method according to the invention renders it possible to incorporate body part data, which contains information about the inner structure of the body part, into the production of the orthopedic product.

A user of the method, such as an orthopedic technician who is carrying out the method according to the invention, can recognize information about the inner structure of the body part in the form of body part data on the display device, for example a monitor, and at the same time see the outer contour and shape of the body part. In this way, they can optimally adapt the shape of the orthopedic device to the information displayed. This occurs during the generation of production data, which preferably occurs virtually. With the help of an electronic data processing device, which preferably also controls the presentation of the data shown using the display device, an orthopedic product can be electronically generated that takes into account the displayed data and the situation of the patient it represents.

In preferred embodiments, which are described in more detail below, the step of generating production data contains additional sub-steps, so that the production data is not generated solely on the basis of the body part data. Preferably, the user of the method, preferably the orthopedic technician, can deform or mold the body part, such as an amputation stump, such that body part data that has been modified from the originally provided body part data is used as a basis for the production data. The user of the method preferably approves the displayed data for the generation of production data.

The production data that is created and generated in this way is then made available to a production center that produces the orthopedic products. For example, this can be achieved by creating a negative mold or a positive mold of an amputation stump on the basis of the production data, said mold being used as a basis for a prosthesis socket to be produced. It is thus possible, for example, to construct a carbon fiber-reinforced prosthesis socket on a positive mold of the amputation stump, for example by applying carbon fiber mats impregnated with a synthetic resin that are subsequently hardened using a known method. Alternatively, the production data can be given to a 3D printer, which then creates a three-dimensional print of the prosthesis socket from a suitable plastic material. In principle, all additive manufacturing processes that can process materials suitable for a prosthesis socket are appropriate.

Alternatively, splint systems, joints, shells or other components of an orthosis can be produced, for example, which take into account the patient's individual circumstances, for example sizes and lengths of certain body parts, such as arms and legs, the position and orientation of various body parts in relation to each other, and movement options and restrictions of joints, for example. This is especially advantageous with shells that are required and fitted directly to a patient's body part and come into direct contact with this body part during subsequent use of the orthopedic products.

It is important that the user of the method sees the body part data, which contains information about the inner structure of the body part, from the current viewing direction or at least almost the current viewing direction as well as the body part. This renders it possible, for example, to display the ends of bones, muscle paths and nerve pathways, and to take these into account during the production of the orthopedic product and the generation of the production data for this product.

The body part may be an arm, such as an upper or lower arm, a leg, such as an upper or lower leg, or a joint, such as a hip joint, a knee, an ankle joint or an elbow. For prostheses and prosthesis sockets in particular, the body part may also be an amputation stump, such as an upper leg stump, a lower leg stump or an arm stump.

The body part data is preferably three-dimensional body part data.

In a preferred embodiment of the method, the body part data is presented via the display device while the user of the method is looking directly at the body part. This is possible, for example, with suitable glasses or goggles (virtual reality—VR—goggles, augmented reality—AR—goggles) or another technical device. It is especially preferable if the display device is partially transparent AR goggles. This means that optical data, particularly the body part data, can be displayed and the user can see the body part through the display device at the same time. A detection device is preferably arranged on the display device that enables the detection of the current viewing direction in which the user of the display device is looking.

Alternatively or additionally, the body part data can also be projected onto the body part itself. The display device is then a projector that projects the body part data onto the body part, for example an amputation stump, preferably along the current viewing direction.

The advantage of these embodiments is that the user of the method, who has so far been using methods known from the prior art in which the body part is pressed and molded directly by hand, does not have to learn a new technique. They can continue to work directly on the body part, looking at their hands and the body part at the same time. It is not necessary to use a separate display device, such as a monitor or a screen.

Alternatively or additionally, image data of the body part is captured using, for example, a camera device. The current viewing direction then corresponds to the viewing direction of the camera on the body part. The user of the method looks at the display device, for example in the form of a monitor or screen, and sees the body part from the perspective of the camera device.

To obtain as realistic an image as possible, the body part data from the current viewing direction must also be displayed on the display device. Since it is body part data, the electronic data processing device is able to calculate which data can be displayed and in what relation to each other.

Alternatively or additionally, image data can also be captured using a scanning device. This may be a scanliner or a scanning glove. For example, if the body part is an amputation stump, a scanliner can be used that is drawn over the amputation stump and is able to capture its own geometric shape. This may be achieved, for example, via strain gauges inside the liner that determine the distance between precisely specified points of the liner. If this occurs across a sufficiently large section of the liner, preferably across the entire liner, the contour and the geometric shape of the liner and thus also the geometric shape and contour of the amputation stump inside the liner can be determined. Alternatively or additionally, scanner gloves can be used with available body parts, such as arms, legs, feet or joints. They feature sensors that can measure and determine absolute positions, for example, so that the geometric shape and outer contour of the body part can be detected and measured in that, for example, the user of the method scans the skin of the body part while wearing a scanning glove.

Corresponding sensors that are used in a scanning glove or scanliner are, for example, fiber Bragg sensors, ultrasound sensors or magnetic sensors by means of which the outer shape of the body part can be detected. This shape can also be updated if the user of the method, for example an orthopedic technician, deforms the body part. This could enable the detection of a contact pressure via pressure sensors, for example.

Image data captured by a scanning device is also referred to as contour data in the following.

If the camera device that captures the image data of the body part is an individual camera, the viewing direction corresponds to the direction from which the camera captures the body part. In addition to the direction from which the camera can record electromagnetic radiation, this also includes the orientation of the body part relative to the camera. The position and orientation of the body part relative to the camera are known, so that both can be positioned in a single coordinate system. This also determined the viewing direction from which the image data is displayed. If the camera device is not an individual camera, but a device with multiple cameras that enables, for example, a three-dimensional capturing of the body part, the viewing direction can be freely or at least almost freely selected. To this end, operating elements may be provided that can be used by the user of the method to change the viewing direction as required.

Preferably, a partially transparent display device is used by way of which image data and/or contour data of the body part can be displayed in addition to the body part data. This image data is consequently detected by the user of the method. Since the display device is partially transparent, the user can also look directly at the body part. It is therefore advantageous if the image data displayed contains additional information. It can preferably be achieved by capturing the image data in a frequency range that is not perceptible by the human eye. For example, an infrared camera can be used to generate a thermal image of the body part, which allows for conclusions to be drawn about the blood circulation in various areas of the body part. Alternatively or additionally, data about blood circulation may also form part of the body part data.

To generate production data, product data is preferably initially generated on the basis of the three-dimensional body part data and/or the recorded image data and/or contour data, on the basis of which the production data is generated. The three-dimensional product data is preferably generated by the electronic data processing device. Even if a partially transparent display device is used through which only the body part data is displayed, it is advantageous in this case to use a camera device to capture image data and/or contour data of the body that is transmitted to the data processing device. The data processing device is therefore able to generate the three-dimensional product data on the basis of the three-dimensional body part data displayed and image data and/or contour data of the body part that is not displayed. However, it is important that the image data is recorded from the current viewing direction.

The user of the method can make changes to the product data. This may be done, for example, by molding or deforming the body part, for example an amputation stump. Alternatively or additionally, the user, such as an orthopedic technician, can apply markers to the body part or highlight areas, for example by using hand gestures, that can be captured by a camera and recognized and processed by an electronic data processing device. This renders it possible, for example, the highlight areas in which padding is to be arranged later. Different materials that are to be used for the produced product can also be assigned to different areas in this manner.

Preferably, the body part data, especially the three-dimensional body part data, has been obtained using a medical imaging process and stored, for example, in an electronic data memory that can be accessed by an electronic data processing device. The medical process may refer, for example, to a CT (computed tomography) procedure, an MRI (magnetic resonance imaging) procedure or another imaging process. This data is often available anyway, as it was captured and recorded after the operation. Alternatively or additionally, corresponding body part data can be recorded within the scope of the method described here and then provided.

Alternatively or additionally, data that has been simulated and calculated using a model can also be used as body part data, particularly three-dimensional body part data. This is not based on actual data of the inside of the current body part; rather, it has been simulated and estimated on the basis of data collections of body parts of other patients, for example.

The body part data, especially the three-dimensional body part data, may also be captured using vibrometry. Such a method, in which mechanical properties of a human body part, especially an amputation stump, are determined comprises the following steps:

a) the human body part is stimulated to oscillate mechanically,
b) the oscillation is recorded by a recording device,
c) the recorded oscillation is evaluated by at least one electronic data processing device, which determines at least one mechanical property of the body part.

This method is based on the knowledge that a number of mechanical properties, such as elasticity, strength and other oscillation properties, can be identified by stimulating the body part to be examined to oscillate mechanically; this oscillation is then recorded and evaluated. Depending on the distribution of, for example, bones and soft tissues within a body part, such as an amputation stump, mechanical oscillations will occur in varying degrees.

The recording device is able to record the mechanical oscillation. This is done by detecting and determining measured values that contain statements about the oscillation behavior of the human body part. For example, this may be the amplitude of a oscillation, the damping behavior and/or the frequency of an oscillation. It is advantageous to not only record the corresponding measured values at one point of the body part, but preferably across a larger area, especially preferably across the entire body part.

To evaluate the mechanical oscillation recorded in this way and determine the mechanical properties of the respective body part, the electronic data processing device preferably has a theoretical model, preferably a three-dimensional model of the body part, for establishing a link between the recorded measured values and the desired properties. For example, the model contains assumptions about position, orientation, size and/or length of bones, muscles or other organs and soft tissue within the body part to be examined. It is especially preferable if the model is based on the information that, for example, can be taken from existing patient MRI data, geometric templates or other sources of information. This includes, for example, an indentation test. Three-dimensional stump data in particular can be used, which has been generated through other methods and/or examination methods and/or models and statistical evaluations.

The recorded oscillations, especially the detected measured values, are transmitted to the at least one electronic data processing device. It processes the data and determines, for example, oscillation durations, eigenmodes or damping behavior, from which the moving masses and stiffness can then be calculated.

In a preferred embodiment, the at least one body part is stimulated to oscillate mechanically by a stimulation device. Alternatively, the body itself can be made to oscillate through conscious or unconscious muscle contractions. However, a reproducible stimulation is achieved by external stimulation devices that act on the body part from outside.

The stimulation device preferably exerts at least one mechanical impulse, in particular a shock, and/or then a mechanical oscillation, for example a vibration, on the body part. In especially preferred embodiments, the stimulation device is able to vary the frequency and/or amplitude of a mechanical oscillation exerted on the body part, rendering these variables adjustable and therefore reproducible. The stimulation device, which is configured to exert mechanical impulses, especially impacts, on the body part, is preferably configured to vary the chronological interval, the strength and/or the duration of the individual mechanical impulses in such a way that these variables are adjustable and therefore reproducible. The mechanical impulse may consist of an impact or other movement of part of the tissue of the body part. While an impact is perpendicular or at least nearly perpendicular to the skin of the body part, for example, a movement nearly parallel to the skin of the body part can also be used as a mechanical impulse, said movement occurring in a lock. Of course, combinations of movement directions are also possible.

In a preferred embodiment of the method, the human body part is successively set into different mechanical oscillations, which are preferably effected by different stimulations from at least one stimulation device. In this way, different eigenmodes, different oscillations and different reactions of the at least one body part to the different stimulations can be generated and studied. Several different measured values can be generated and therefore a more detailed model used. In particular, when detecting and examining eigenmodes, which may be present, for example, in the form of standing oscillation waves, especially if the stimulation device causes the at least one body part to oscillate permanently, oscillation nodes may also be present in which the soft tissues of the respective body part do not move or only move minimally at this point. It is therefore advantageous to examine different oscillations of the human body part in order to also create oscillations at the points that are arranged in oscillation nodes during a first oscillation, which can be examined.

It is therefore advantageous that the stimulation device of the at least one body part stimulates at at least two different positions and/or at several times. By using multiple stimulation positions, various oscillations can be generated and observed, as already explained. This improves and expands the database on the basis of which the mechanical properties of the body part are determined, thereby allowing more detailed models to be used. Due to the repeated stimulation of the same oscillation, which is generated, for example, by consecutively stimulating a body part multiple times in an identical manner at the same position, multiple measurements of the same oscillation are conducted, thereby improving the measurement result and quality of data.

The detection device preferably features at least one optical detector, in particular at least one camera. It is especially preferable if the detection device features multiple optical detector, in particular multiple cameras, so that the respective oscillations is detected from different directions. This renders it possible, for example, to detect the amputation stump in its entirety, i.e. particularly in 3D. The at least one optical detector, particularly the at least one camera, is pointed at the examined body part, i.e. preferably the amputation stump, and detects the oscillations that occur. Via image recognition software, the images captured in this way can be used to detect and read various oscillation modes, frequencies and/or amplitudes. These can be added to the model, so that the desired mechanical properties can be calculated.

It is especially preferable if the at least one body part is irradiated with detection radiation, whose reflection on the body part is detected by the detection device. The detection beam is preferably electromagnetic radiation, especially preferably laser radiation. The detection radiation is directed onto the body part to be observed, where it is reflected. In the case of monochromatic laser radiation in particular, this changes the wavelength due to the Doppler effect when it is reflected by a moving object If the point of the body part where the laser radiation strikes moves, the frequency of the laser radiation increases at the moment it strikes the optical detector. If the point moves away from the optical detector, the frequency decreases. It is therefore possible to generate an image of the amputation stump or the at least one body part, the frequency of the reflected laser radiation being displayed as a function of the point of impact in each case. In this way, a velocity image, i.e. a distribution of the respective velocity and thus of the oscillation, can be displayed.

In a preferred embodiment, the at least one body part features a marker. The shape, size, direction and arrangement of the marker is preferably stored in an electronic data storage device of the at least one electronic data processing device. It is consequently known what the marker looks like when at least one body part is not made to oscillate. If the body part is stimulated to oscillate, at least the skin, where the marker is located, begins to move, preferably also causing the marker to move. However, since the skin is not moved homogeneously when the at least one body part is made to oscillate, displacements, distortions and deformations occur with the marker that can be detected or evaluated.

Preferably, the at least one marker is applied to the body part, especially stuck, sprayed on or applied in the form of a coat or label. The body part with the applied marker is then measured, for example detected by the detection device, without it having been made to oscillate. Alternatively or additionally, a marker can be projected onto the body part by, for example, exposing it to strip lighting. This means that the body part is not illuminated over the entire surface, but with a pattern of light and dark areas, which can also be detected by the at least one detection device. Even if the marker, i.e. the lighting itself, is not altered by the oscillations, the position, location and orientation of individual sections of skin of the at least one body part relative to the light source do change, so that the body part moves relative to the marker. This also causes a change in the arrangement of the illuminated and non-illuminated areas on the body part, which can be detected and evaluated.

The mechanical property detected by the method described here preferably contains the location and/or the position of at least one internal tissue and/or organ areas, a material structure, an elasticity and/or oscillation damping. It is especially preferable if the human body part is an amputation stump.

Preferably, the three-dimensional product data is displayed by means of the display device. It is especially preferable if it is displayed superimposed on the body part data.

The body part data, especially the three-dimensional body part data, preferably contains information about bones, muscles, nerves, blood vessels and/or soft tissue of the body part. This relates to the location, orientation and course of the corresponding parts.

Prior to generating the production data, the body part is preferably deformed and/or molded, wherein correspondingly modified image data is displayed via the display device. The deformation of the body part can be done manually by the orthopedic technician, for example. The experience gained in previous procedures using molding via plaster can thus also be used in the new method. The orthopedic technician creates the desired shape of the body part. If a camera device is used, it captures the image data. This image data, which is altered in accordance with the deformation of the body part, is displayed by means of the display device. In this way, virtually displayed and preconstructed orthopedic products can be adapted to the altered dimensions and shapes of the respective body part.

Preferably, an electronic data processing device calculates, by means of an underlying model, the effects of the deformation and/or molding of the body part on the internal structure of the body part. For example, this relates to the displacement or movement of bones and muscles, the course and/or length of which may change due to the deformation and/or molding of the body part. Soft tissues can be compressed, changed in shape or displaced by the deformation of the body part. In the preferred embodiment, all of these changes that occur due to the deformation of the body part are calculated by the electronic data processing device. On the basis of the results of this calculation, the body part data is modified and displayed on the display device in this modified form. The modified body part data is now displayed superimposed on the altered image data, so that the orthopedic technician can directly examine the effect and result of their deformation and/or molding of the body part. They are no longer limited to their experience or senses, but can check whether their deformation and/or molding of the body part has the desired effect. If this is not the case, they can correct it and perform another deformation and/or molding of the body part. Preferably, modified three-dimensional product data is also generated on the basis of the modified body part data and/or the altered image data, the production data being generated on the basis of said product data.

As previously explained, the deformation and/or molding of the body part is detected by means of at least one scanning glove and/or a scan liner.

Preferably, after generating the production data, the effects of a load and/or a movement of the body part when the orthopedic product is mounted on the body part are simulated and the result of this simulation is displayed by means of the display device. In this way, it is checked whether the production data results in an orthopedic product that meets the requirements and ensures sufficient wearing comfort and functionality at the same time. This is preferably done by means of the electronic data processing device, which uses a model to simulate occurring loads and/or possible movements of the body part. This determines where, for example, particularly high pressures or frictions occur under certain loads and/or during certain movements, which can lead to pain and wounds, or at least significantly reduce wearing comfort.

The data calculated in this way provides information on the loads within a gait cycle, for example. The user of the method, in particular an orthopedic technician, is then able to alter the product data and production data and adapt them to the dynamic circumstances. Ideally, this renders the production of a test product, such as a test socket for checking under strain, unnecessary, so that the final product can be produced directly.

Additionally or alternatively, movements of the body part, especially an amputation stump, can be detected by means of a camera device and/or a scanning device. These movements can then be simulated, so that the electronic data processing device can calculate the effect of these executed and executable movements on the body part data, especially if the orthopedic product has already been produced according to the existing production data and then worn. This includes loads and movements that are particularly important when the orthopedic product affects a joint of the wearer.

The direction of view can preferably be adjusted. This is especially advantageous if, for example, individual elements of the inner structure of the body part can only be seen from different directions of view. Alternatively or additionally, changing the direction of view is advantageous in order to optimally adapt the prosthesis socket to be produced to the body part in as many directions as possible. Changes in the shape of the body part when viewed from different directions can also cause different changes in the inner structure and thus require different modifications of the body part data.

In a preferred embodiment of the method, the direction of view is calculated from a location and orientation of the body part relative to the camera device, in particular a camera. This may occur in various ways. For example, if the position and orientation of the at least one camera with the camera device is known, this position and orientation can form the basis of the calculation. If the position and orientation of, for example, a bracket or plate in which the body part is held or on which it rests is known, these two positions and orientations can be used to calculate the direction of view.

It is especially preferable if the location and orientation of the body part relative to the camera device is calculated from the captured image data, wherein the body part preferably features at least one marker, especially a sticker and/or label. The camera device comprises at least one camera that captures the body part and records the image data. If the shape of the body part is known, image recognition software in the electronic data processing device can be used, for example, to calculate the orientation and location of the body part in relation to the camera and how far away it is from the camera. In this way, all data for determining the direction of view is known. Alternatively or additionally, at least one marker can be arranged on the body part. If this is done at previously defined points, it is possible to determine the position and orientation of the markers, for example at least one sticker, from the recognized image data and thus to determine the position and orientation of the body part relative to the camera from the known position of the markers on the body part. The direction of view can be also be clearly determined in this manner.

The invention also solves the problem by way of a method for generating production data for an orthopedic product that can be used in a method of the type described here. The actual adaptation of the product to the body part takes place until the production data is generated. This can then be transmitted to a conventional production site, which is not necessarily identical to the place where the previous process steps are carried out. In this way it is possible, for example, to transmit data electronically, especially wirelessly, via networks such as the internet to the production site, which can be located almost anywhere in the world.

The invention also solves the problem by way of a method for displaying body part data, in particular three-dimensional body part data, that can be used in one of the methods described here. The body part data is displayed in such a way that a user of the method sees both the body part data and the body part itself superimposed. They see both the body part and the body part data from the current direction of view.

Such a method allows, for example, an orthopedic technician to adapt a previously produced orthosis to the patient's individual conditions and needs and, for example, to adapt, adjust or displace joint axes, joint positions and/or joint orientations. In this method, it is also advantageous if changes that are made, for example, to the orthosis and/or the body part and that have an influence on the interior of the body part are recorded and processed by the electronic data processing device. The electronic data processing device is therefore preferably able to model the influence of these changes, adjust the body part data accordingly and display the body part data adjusted in this way.

The invention also solves the problem by way of a device for conducting a method as described here, wherein the device comprises at least one camera device, at least one display device and at least one electronic data processing device.

In a particularly preferred embodiment, the camera device and the display device are parts of a single device, which is to be arranged on the user's head. For example, this may be glasses/goggles, particularly VR goggles (VR=virtual reality), AR goggles (AR=augmented reality) or a suitable hood or helmet. Such a device makes it especially easy for the user of the device wishing to carry out the method to observe the amputation stump from different perspectives and design the prosthesis socket accordingly.

BRIEF DESCRIPTION OF THE DRAWINGS

In the following, some examples of embodiments of the present invention will be explained in more detail by way of the attached figures: They show FIGS. 1 and 2—schematic representations of process sequences and FIG. 3—the schematic representation of image data and three-dimensional body part data.

DETAILED DESCRIPTION

Figure 1:
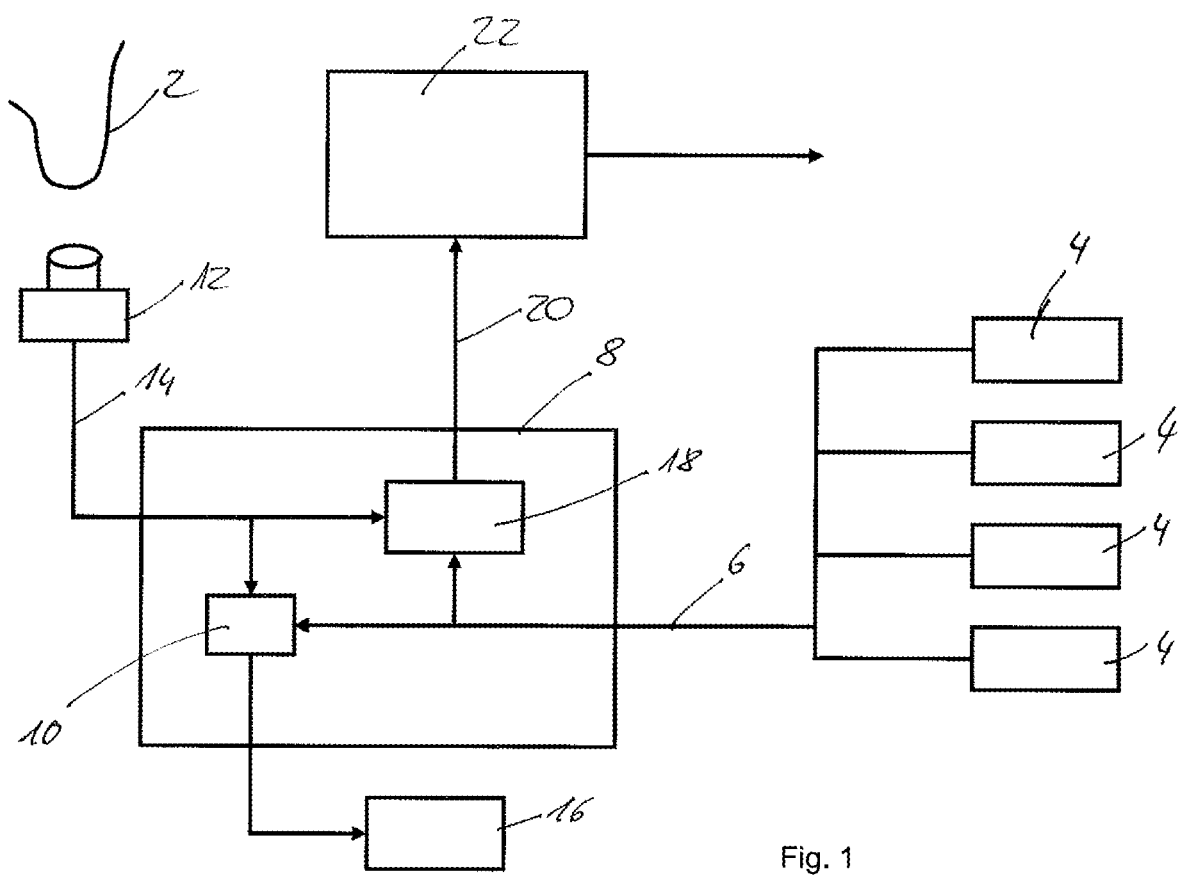

FIG. 1 schematically depicts a structure and process sequence as can be used for an embodiment of the present invention. An orthopedic product is to be created for a schematically shown body part 2, which is depicted as an amputation stump. To this end, body part data 6 is first provided via medical procedures 4, for example. A wide variety of medical procedures 4 can be used. Different medical procedures 4 are shown, each of which is depicted schematically. Of course, more or fewer medical procedures 4 can be used to provide body part data 6.

Body part data 6 is supplied to an electronic data processing device 8, which features a display module 10. The body part data 6 is transmitted to this display module. The body part 2 is also captured by a camera device 12. It sends image data 14 to the electronic data processing device 8, in particular to the display module 10. The camera device 12 captures the body part 2 from the current direction of view. The camera device 12 may be based on visible light, UV light or infrared waves, and record corresponding images of the body part 2.

The display module 10 of the electronic data processing device 8 is configured to create a common image from the body part data 6 and the image data 14 made available to it and to display them superimposed. For this purpose, the device features a display device 16, for example a monitor. The display module 10 recognizes or knows the current direction of view and also displays the body part data 6 transmitted to it from the current direction of view in such a way that a user of the method, not depicted, is shown the body part data 6 and the image data 16 superimposed on the display device 16 from the same current direction of view.

The body part data 6 and the image data 14 are also transmitted to a generation module 18 of the electronic data processing device 8. On the basis of the transmitted data, it generates production data 20, which is transmitted to a production site 22. This may be a 3D printer, for example, or another production device.

Figure 2:
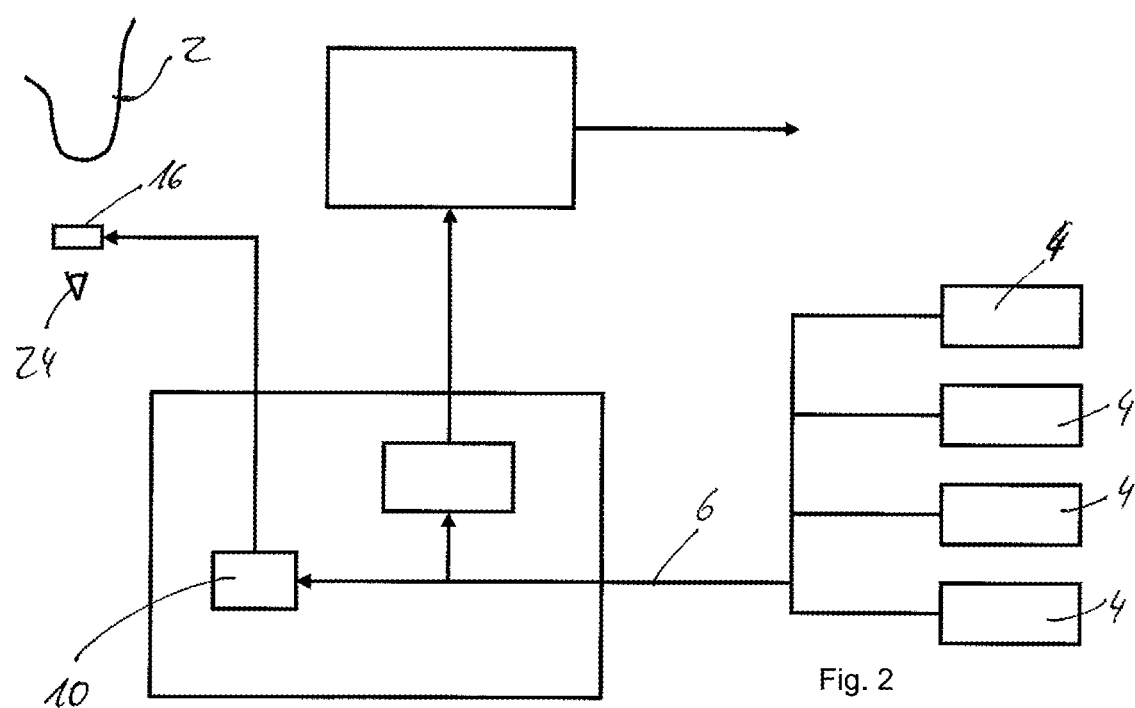

FIG. 2 depicts another embodiment, which differs from the embodiment shown in FIG. 1 in one detail only. The body part 2 is not observed by a camera device 12, but by the user 24 of the method, schematically depicted as an eye. They are looking through the display device 16, for example AR goggles. The display device 16 is designed to be partially transparent, so that the user 24 sees both the body part 2 and the data provided by the display module 10. However, this only refers to body part data, particularly three-dimensional body part data 6 that has been determined and provided by the various medical procedures 4. Both in the process according to FIG. 1 and in the process according to FIG. 2, the body part data 6 is of course not provided directly by the medical procedures 4. Rather, they are created by the medical procedures 4 and stored in an electronic data storage device, not shown, which can be accessed by the electronic data processing device 8.

Figure 3:
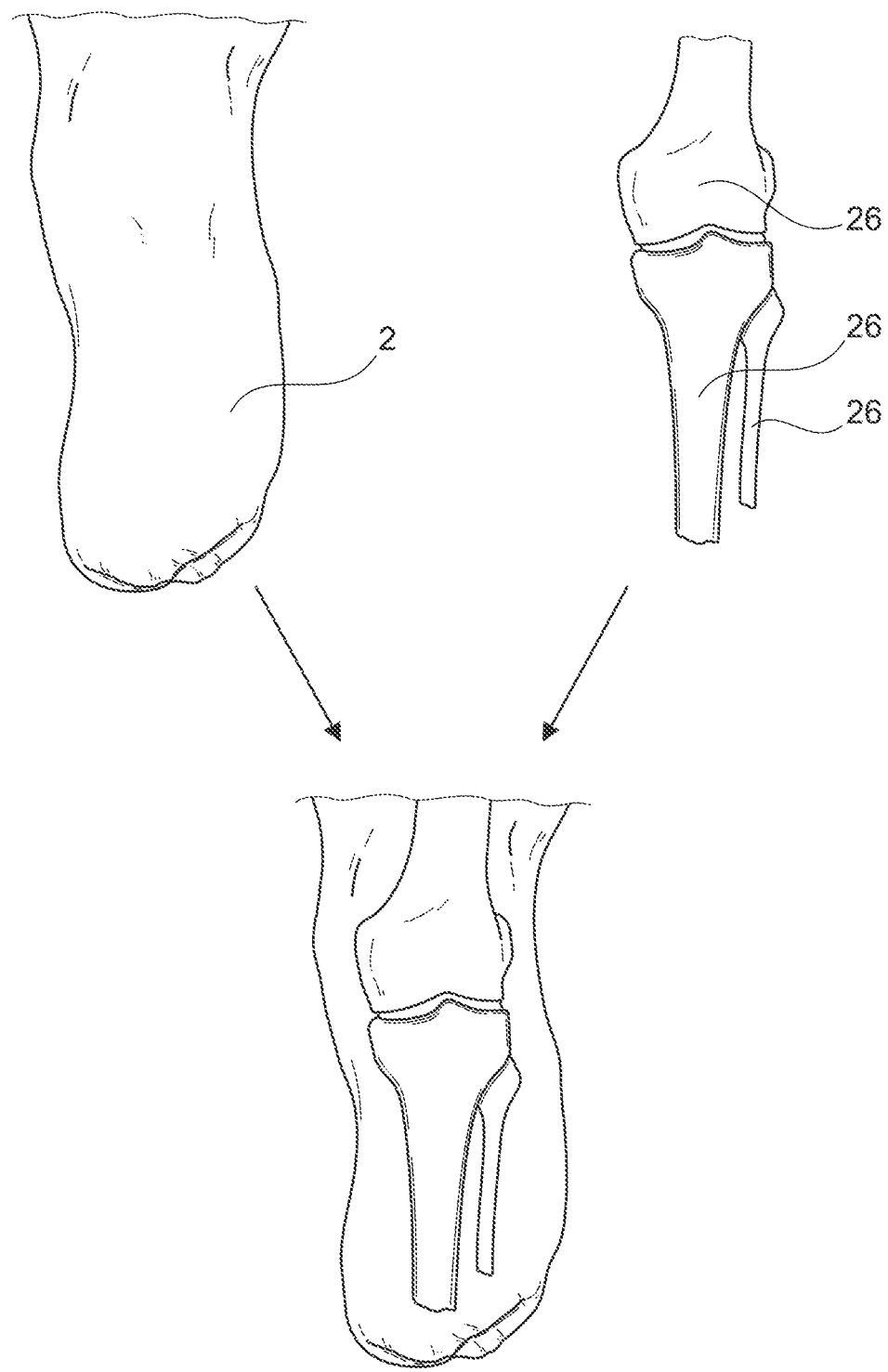

FIG. 3 schematically depicts the various data, which is shown superimposed. In the upper left area of FIG. 3, image data 14 of an amputation stump, i.e. a body part 2, is shown. In the upper right area, the bones 26 found in the interior of the body part 2 are depicted. This data has been generated by an MRI procedure, for example, and is stored in an electronic data storage device. It is therefore three-dimensional body part data 6. In the lower area of FIG. 3, the image data 14 and the three-dimensional body part data 6 are shown superimposed, as would be the case on the display device 16, for example, in the arrangement shown in FIG. 1.

REFERENCE LIST 2 body part
4 medical procedure
6 body part data
8 electronic data processing device
10 display module
12 camera device
14 image data 16 display device
18 generation module
20 production data
22 production site
24 user
26 bones

The invention claimed is:

1. A method for producing an orthopedic product for a body part of a patient, the method comprising the following steps:
   a) providing body part data that contains information about an inner structure of the body part,
   b) detecting a current direction of view from which a user of the method sees the body part,
   c) presenting the body part data from the current direction of view by means of a display device, so that the user sees the body part and the body part data superimposed,
   d) generating production data for the orthopedic product on the basis of the data displayed, and
   e) providing an orthopedic product produced on the basis of the production data, wherein prior to generating the production data, the body part is preferably deformed and/or molded and an electronic data processing device uses a model to calculate the effects of the deformation and/or molding of the body part on the inner structure of the body part and modifies the body part data accordingly, wherein the modified body part data is then displayed.

2. The method according to claim 1, characterized in that the body part data is three-dimensional body part data.

3. The method according to claim 1, wherein the display device is partially transparent, so that the user can look through the display device.

4. The method according to claim 1, wherein image data of the body part is captured by means of a camera and/or a scan device at least also from the current direction of view, said image data being displayed superimposed on the body part data by means of the display device.

5. The method according to claim 1, wherein, in order to generate the production data, three-dimensional product data is initially generated on the basis of the body part data and/or captured image data, on the basis of which the production data is generated.

6. The method according to claim 1, wherein the body part data has been obtained by a medical imaging process or is obtained as part of the method prior to its provision.

7. The method according to claim 5, wherein the three-dimensional product data is displayed using the display device, wherein it is preferably shown superimposed on the body part data.

8. The method according to claim 1, wherein the body part data contains information on bones, muscles, nerves, blood vessels and/or soft tissues of the body part.

9. The method according to claim 1, wherein three-dimensional product data adapted to the deformation and/or molding is generated in order to generate the production data.

10. The method according to claim 1, wherein the deformation and/or molding of the body part is captured by means of at least one scanning glove and/or scan liner.

11. The method according to claim 1, wherein, after generating the production data, the effects of a load and/or a movement of the body part when the orthopedic product is in mounted state on the body part are simulated and the result of this simulation is displayed by means of the display device.

12. The method according to claim 1, wherein the direction of view can be changed.

13. The method according to claim 1, wherein the direction of view is calculated from a position and orientation of the body part relative to the camera device, in particular a camera.

14. The method according to claim 13, wherein the position and orientation of the body part relative to the camera device is calculated from the captured image data, the body part preferably featuring at least one marker, particularly a sticker and/or label.

15. A method for displaying body part data for use in a method according to claim 1 in which body part data is displayed in such a way that a user of the method sees the body part data and the body part superimposed from the current direction of view.

16. The method according to claim 15, wherein the camera device and the display device fom1 part of a device to be arranged on a head of a user, especially glasses/goggles, a hood or a helmet.

17. A method for conducting a method according to claim 1, the device comprising at least one camera device, at least one display device and at least one electronic data processing device.

18. A method for producing an orthopedic product for a body part of a patient, the method comprising the steps of:
   providing three-dimensional body part data that contains information about an inner structure of the body part;
   detecting a current direction of view from which a user of the method sees the body part; presenting the body part data from the current direction of view by means of a display device, so that the user sees the body part and the body part data superimposed, wherein the display device is partially transparent;
   generating production data for the orthopedic product from the data displayed; and providing an orthopedic product produced from the production data, wherein prior to generating the production data, the body part is preferably deformed and/or molded and an electronic data processing device uses a model to calculate the effects of the deformation and/or molding of the body part on the inner structure of the body part and modifies the body part data accordingly, wherein the modified body part data is then displayed.

* * * * *